(12) United States Patent
Shoenfeld

(10) Patent No.: US 7,728,711 B2
(45) Date of Patent: Jun. 1, 2010

(54) REMOTELY OR LOCALLY ACTUATED REFRIGERATOR LOCK WITH TEMPERATURE AND HUMIDITY DETECTION

(75) Inventor: Norman A. Shoenfeld, Livingston, NJ (US)

(73) Assignee: S&S X-Ray Products, Inc, Pen Argyl, PA (US)

( * ) Notice: Subject to any disclaimer, the term of this patent is extended or adjusted under 35 U.S.C. 154(b) by 498 days.

(21) Appl. No.: 11/653,726

(22) Filed: Jan. 16, 2007

(65) Prior Publication Data

US 2007/0125100 A1    Jun. 7, 2007

Related U.S. Application Data

(63) Continuation-in-part of application No. 11/391,986, filed on Mar. 29, 2006, now abandoned.

(51) Int. Cl.
 *B60R 25/00* (2006.01)
(52) U.S. Cl. .................. 340/5.73; 700/237; 700/244; 70/275; 702/127; 702/187; 340/5.7; 340/5.2; 340/5.1; 340/825
(58) Field of Classification Search .................. 62/441, 62/440, 125, 126; 700/237, 232, 231, 213, 700/90, 236, 242, 244; 70/85, 77, 57, 264, 70/263, 262, 266, 267, 277, 275, 280; 221/15, 221/154, 2, 3; 340/309.15, 568.1, 540, 500, 340/5.73, 5.7, 5.2, 5.1, 825; 368/10; 702/177, 702/176, 127, 187
See application file for complete search history.

(56) References Cited

U.S. PATENT DOCUMENTS

| | | | | |
|---|---|---|---|---|
| 5,572,873 A | * | 11/1996 | Lavigne et al. | 62/3.62 |
| 6,788,997 B1 | * | 9/2004 | Frederick | 700/236 |
| 2005/0077806 A1 | * | 4/2005 | Schellenberg | 312/400 |
| 2007/0150554 A1 | * | 6/2007 | Simister | 709/219 |

* cited by examiner

*Primary Examiner*—Brian A Zimmerman
*Assistant Examiner*—Kevin Lau
(74) *Attorney, Agent, or Firm*—Bernard P. Molldrem, Jr.

(57) ABSTRACT

A remotely or locally actuable refrigerator door lock has a body portion that is attached to the cabinet and a door portion that is attached to an edge of the door. A latch in the body portion engages a strike plate in the door portion and can be lifted out of engagement to open the refrigerator. The door lock assembly may be connected to a touch-screen device or via a USB or ethernet connection to a remote host computer. The host computer keeps an audit trail of the times and personnel accessing each refrigerator, and a temperature audit trail. The system may be used in hospital for controlling access to pharmaceuticals or may be used in a weight loss program. Temperature and humidity sensors are positioned within the refrigerator cabinet. The door lock may have battery power for portable or mobile applications.

2 Claims, 5 Drawing Sheets

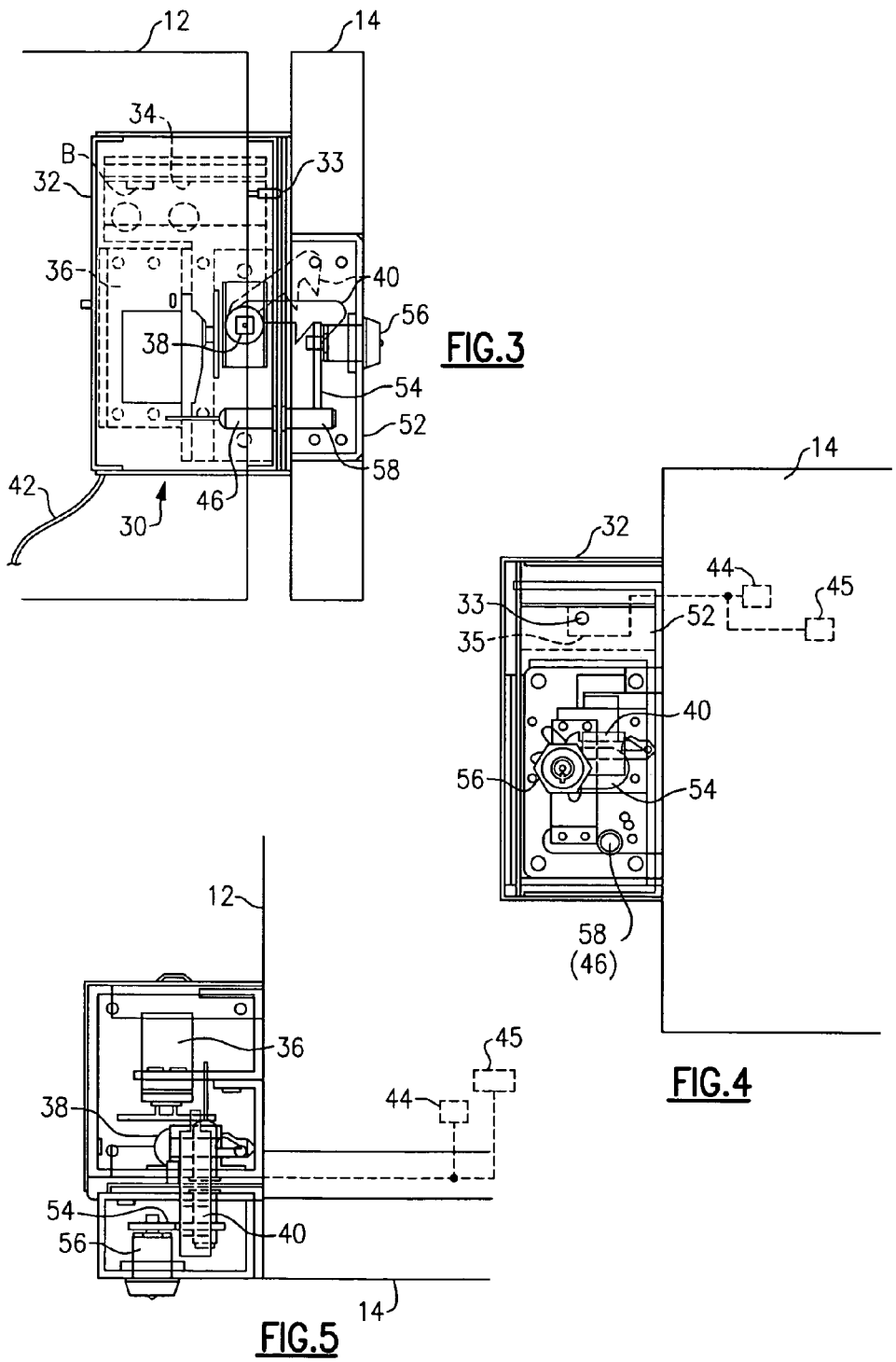

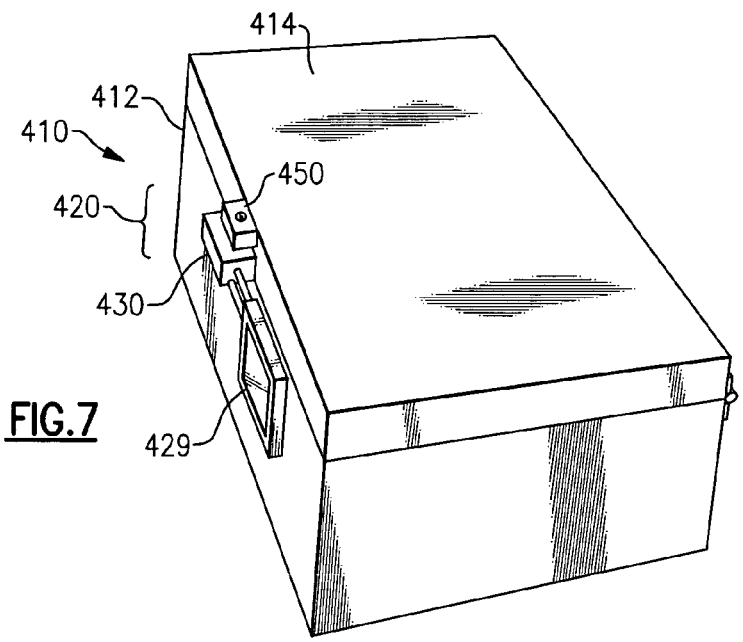
FIG.7
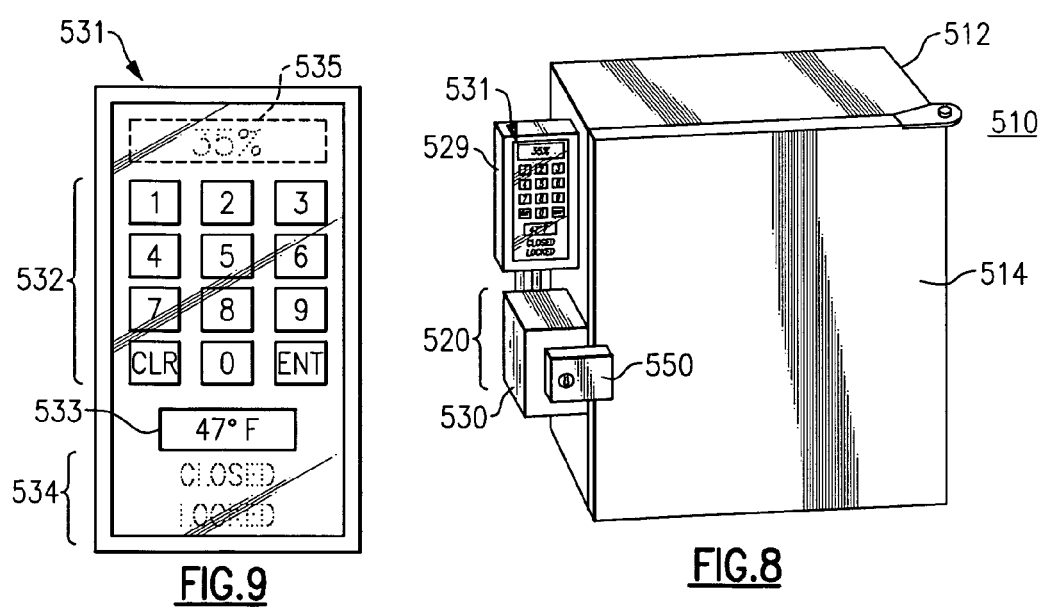
FIG.9
FIG.8

REMOTELY OR LOCALLY ACTUATED REFRIGERATOR LOCK WITH TEMPERATURE AND HUMIDITY DETECTION

This is a continuation in part of my U.S. patent application Ser. No. 11/391,986, filed Mar. 29, 2006 now abandoned.

BACKGROUND OF THE INVENTION

This invention relates to an electronic lock that mounts on the front door of a refrigerator to limit access to the refrigerator. The invention is more specifically directed to a refrigerator door lock that connects to a remote computer system, e.g., in a hospital or health care facility, to secure pharmaceuticals that need to be refrigerated, and to facilitate keeping an audit trail of access to the refrigerator. The invention may also be employed as an adjunct to a weight loss program. The lock may also be used in connection with a warming cabinet for ingestible materials or injectable materials such as contrast agents for radiography, where the materials need to be kept at body temperature.

In general, pharmaceuticals are delivered to patients when needed, and those that need to be kept refrigerated are stored in a refrigerator in the pharmacy of the hospital or other facility. However, it is more convenient and better use of the nurse's time and efforts to keep the pharmaceuticals at the patient locations, i.e., in the patient's room or ward, or in the cluster of rooms where the patient is located. However, those drugs that need refrigeration cannot simply be stored in a secured dispensing cabinet at the room or nurse station, but have to be kept in a refrigerator until needed. The refrigerator is either unsecured, or is kept locked with a key lock, with the key distribution limited only to certain persons in the nursing staff and pharmacy staff. Any record of access to the refrigerator would have to be maintained on a paper record, or by separately keying in information on separate computer work station. There is also no means provided to ensure that the refrigerator is kept locked, to alarm if the refrigerator is left open or unlocked, or to monitor the refrigerator's operating temperature. In the current systems, there is no means provided to warn the pharmacy department or the nursing staff if the refrigeration cabinet has failed to maintain the materials at the chilled temperature, or if the refrigeration or other storage cabinet has failed to maintain the proper relative humidity.

It would be desirable to employ a refrigerator as a pharmacy cabinet at the patient location in which medications that have been prescribed for a patient can be loaded by pharmacy staff and stored securely until administered to the patient, which will automatically keep track of access to the refrigerated cabinet, and which can be accessed by the nurse staff electronically (e.g., using wireless means). It is also desirable to ensure that the refrigerated cabinet is kept secure, and that the operating temperature is sufficiently cool. However, no measure exists, up to the present, to carry this out.

In addition to temperature monitoring, some pharmaceuticals need to be monitored for humidity, and some for both temperature and some for both temperature and humidity when stored.

Also, some medicaments and medical products need to be stored at a temperature above ambient. For example, radiographic contrast materials need to be stored at body temperature (i.e., 37° C.), and these substances are classified as pharmaceuticals and need to be kept in a locked cabinet. The contrast materials are controlled like other pharmaceuticals, and so it is desired to limit access to these materials as well, and to create an audit trail of which persons have access to them. Accordingly, there is a need for a locked warming cabinet that creates an audit trail and which can be monitored for temperature. Controlling access to the contrast materials also limits incidents of contamination or suspected contamination of other pharmaceutical materials. Other controlled materials could be stored at elevated temperatures above or below 37° C., as need be.

For transport of pharmaceuticals, or for use of pharmaceuticals in a mobile situation, there is a need for a refrigerator or storage cabinet lock that operates under battery power so that the pharmaceuticals can be monitored (e.g., for temperature and/or humidity) during transport. Then, if the temperature or humidity was outside the acceptable range during shipping, it will be possible to deny access to the cabinet and to the possibly tainted medication, except for specially authorized supervisory personnel.

It is also desired to track the temperature of the refrigerator or other temperature-controlled cabinet, and automatically provide an alert warning if the temperature (or relative humidity) is outside an acceptable range.

A further need is for ensuring patient safety, i.e., to ensure drugs that have not been kept at the proper storage conditions, e.g., outside of an acceptable temperature range, are not administered to patients until their purity has been checked out by pharmacy staff.

The pharmaceutical industry has achieved a global reach an impact, with medicines and vaccines being shipped to all areas of the world. Many of these medicines and vaccines are temperature sensitive and have precise storage requirements. Unfortunately, during shipment the products can be subjected to extreme temperature and humidity changes, unforeseen delays during transit, especially international transit, and need for field delivery to remote points of use, which often requires several mode changes. In addition, the pharmaceutical companies are subject to relentless cost pressures, so there is a need to make shipping and distribution as efficient as possible while ensuring that the products that are delivered are of consistent quality.

At the present time, most refrigerated medications are shipped in twelve-inch by twenty-four-inch insulated boxes, with ice. These can include a digital thermometer device that logs the temperature, but does not lock the box closed, and does not guarantee that any medication in the box that was subject to poor temperature control is isolated and not distributed to a patient. Some medications are shipped in a box or crate without ice, and are shipped in a refrigerated container. These boxes may have a special security tape that is intended to reveal tampering, but these are not locked containers, and there is no means included to prevent distribution of the medications if they had been subjected to adverse temperature (or humidity) conditions.

A similar problem exists for selectively locking and unlocking a food storage refrigerator and/or warming cabinet at specific meal times in a weight loss or weight control problems.

OBJECTS AND SUMMARY OF THE INVENTION

Accordingly, it is an object of the present invention to provide a remotely or locally actuated refrigerator door and/or warming cabinet door locking arrangement that avoids the drawbacks of the prior art.

It is another object to provide a locking refrigerated cabinet and/or warming cabinet and keeps track of the identity or persons accessing the refrigerator or cabinet and times of such access, for any given medical refrigerator or for each of a number of refrigerators or refrigerated cabinets throughout a facility that are provided with similar remotely actuated door locks.

It is still another object to provide a refrigerator door lock and/or warming cabinet door lock that senses whether the door is open or closed, signals a remote computer system about the open/closed status of the door, and provides status of the interior temperature of the refrigerator or cabinet.

A further object is to provide an audible indication, e.g., with a sounder contained in the door lock enclosure, when the refrigerator door has been kept open longer than a predetermined, programmed time limit.

Another object is to provide the electronic door lock mechanism with a key lock override that can be used, e.g., during a power outage, to obtain access to the medications kept in the refrigerator.

It is another object to provide monitoring of temperature and/or humidity within the cabinet.

A still further object is to provide a refrigerator lock which is suitable for use in shipping of pharmaceuticals in a mobile refrigerated cabinet, with its temperature monitoring capabilities.

In accordance with an aspect of the present invention, a refrigerator is provided with a remotely opened lock, where the refrigerator is used for storing medications or other substances where access has to be controlled. The lock is opened electronically, e.g., using a USB or ethernet cable or similar serial cable device that is connected to a computer or computer network. The lock may include a temperature detector to monitor whether the temperature level inside the refrigerator cabinet is acceptable for the stored pharmaceuticals or other perishable products. In combination with the lock device, software which may be in the lock assembly itself or in a local or remote computer system, keeps an audit trail of when the refrigerator was opened, and who opened it. The same software and network can control multiple locks on different refrigerators throughout a facility, i.e., nursing home, hospital, or other health care facility.

In other embodiments, the lock can be adapted for use in a warming cabinet where materials, such as radiographic contrast materials, are being stored, and where access needs to be limited, and where an audit trail is desired.

According to one preferred embodiment, a remotely actuable refrigerator door lock arrangement locks and unlocks a refrigerator cabinet. The lock arrangement has a body portion that mounts onto the body of the refrigerator cabinet and a door portion that mounts onto the door or the refrigerator cabinet aligning with the body portion when the refrigerator door is closed. The door portion has an enclosure that mounts to the door, with a latch strike member, i.e., latch strike plate, situated within the enclosure. The lock body portion likewise has an enclosure that mounts onto the body of the refrigerator cabinet. A latch member projects from the enclosure to engage the latch strike member. A motor drive mechanism, which may include a servo motor, moves the latch member from an engaged or lowered position, in engagement with the latch strike member, to a released or raised position out of engagement with the latch strike member so as to unlock the refrigerator. A USB cable extends from the enclosure of the body portion to connect, either directly or via a network, with a computer system. An electronics circuit board within the enclosure of the body portion has circuitry for communicating over the USB cable with the computer system, and has circuitry, e.g., a microprocessor, e.g., suitably programmed circuit means for receiving and interpreting commands specific to that specific refrigerator door lock to actuate the motor drive and move the latch member out of engagement with said latch strike member, and thus providing authorized access to the pharmaceutical refrigerator. The door portion may also have a key lock cylinder that is mechanically coupled to the latch strike member, so that the lock can be manually opened, by moving the latch strike member out of engagement with the latch member.

In a preferred arrangement, the latch member has a slant distal surface for moving the latch member over the strike member when the refrigerator door is pushed to its closed position, and also has a recess proximal of that slant surface for engaging said latch strike member so it remains in locked engagement until the latch member is lifted to the release position.

A magnetic (or other equivalent) sensor mechanism within the door lock senses the open/closed state of the refrigerator door. In one embodiment, the sensor mechanism includes a magnet positioned in the enclosure of the door portion and a magnetic sensor portion positioned in the body portion to sense the presence of the magnet when the refrigerator door is closed. The door lock can also incorporate a sounder device that actuated when the door lock has been sensed to be in its open state longer than a predetermined time limit.

An LED (which may be a two-way Red/Green LED) or other visible indicator can be situated on the door portion of the lock, serving as a visible indication of the open/closed status of the refrigerator door lock.

The remote (or local) computer system preferably employs software assigning a respective serial number code to each individual refrigerator door lock permitting said remote computer system to lock and unlock independently each of a plurality of door locks similarly connected with said remote computer system. The software can also include audit trail programming for recording time of opening of each refrigerator door lock connected with said remote computer system and also recording identity of each requesting person associated with such openings of the refrigerator door lock. The software also keeps a time record of the temperature (and/or relative humidity) inside the refrigerator cabinet.

When the software determines that the temperature in a given refrigerator has varied outside of the preset limits, the system will deny electronic access to the medical personnel, e.g., by preventing the motor from lifting the latch member. Then only pharmacy personnel (by means of an over-ride code, or by use of a physical key) can open the unit.

The pharmacy staff can distribute the various patient prescription orders e.g., during non-busy hours, and deposit the temperature sensitive medications into the patient refrigerator. Then the medications are ready for the nurse or other care giver to administer on schedule.

Similar refrigerator or temperature controlled cabinets may be used in the radiology laboratory for controlled storage of items such as radiology contrast materials of or other temperature-sensitive pharmaceuticals.

The refrigerator may be a stand-alone unit with the refrigerator lock of this invention and a self-contained LCD touch-screen display and control computer interface device. Such an embodiment can optionally be connected, e.g., via USB, ethernet, or wireless device, to another computer or computer network, and can provide an audit trail of access. This stand-alone configuration may be useful in a smaller medical office or clinic.

For a mobile or portable use, i.e., for transporting or shipping pharmaceutical materials, the lock mechanism can be adapted to work under battery power, so that the storage conditions for the pharmaceuticals can be monitored during shipping. If the temperature and/or humidity is outside of the acceptable range during shipping, the lock may automatically deny access except to specially authorized pharmacy personnel. This feature can prevent distribution of potentially contaminated or spoiled items. In an embodiment for this use, the lock may be used in combination with a passive shipping container, i.e., an insulated box containing ice or a box without ice intended to be transported in a refrigerated truck. The lock can generate an ID code, which the recipient enters into the shipper website to obtain an opening code sequence. If the shipment has been maintained under acceptable humidity and temperature conditions, the code sequence will permit the recipient to open the lock and access the contents of the shipping box. However, if the contents have been subjected to extreme temperatures or humidity changes, the entry of the ID code will instead return instructions to return the box to the shipper, and the recipient will be denied access. After the box is returned to the shipper, the shipper can obtain an audit trail of the time versus temperature and humidity conditions, and can identify the source of the problem.

The above and many other objects, features, and advantages of this invention will become apparent from the ensuing description of a selected preferred embodiment, which is to be considered in connection with the accompanying Drawing.

BRIEF DESCRIPTION OF THE DRAWING

FIG. 3 is a side view of this embodiment

FIG. 4 is front view of this embodiment.

FIG. 5 is a top view of this embodiment.

FIG. 7 shows an embodiment of this invention in a mobile or portable refrigeration storage implementation.

FIG. 8 shows a stand-alone embodiment, with touch-screen device.

FIG. 9 shows a portion of the embodiment of FIG. 8.

DETAILED DESCRIPTION OF THE PREFERRED EMBODIMENT

Figure 1:
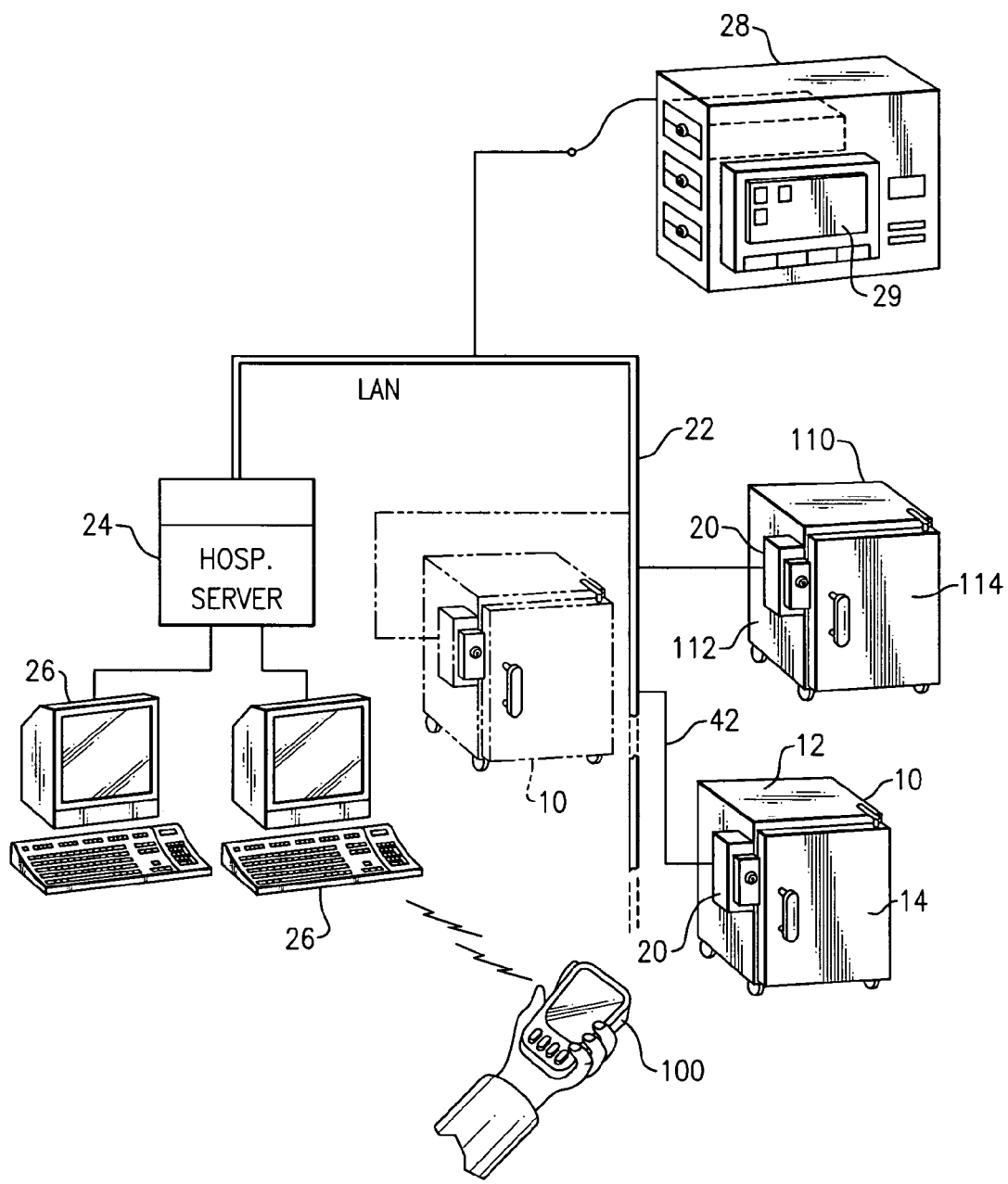
FIG. 1 is a schematic view of a network-connected system including medication storage refrigerator(s) with the door lock arrangement according to one preferred embodiment of this invention.
Figure 2:
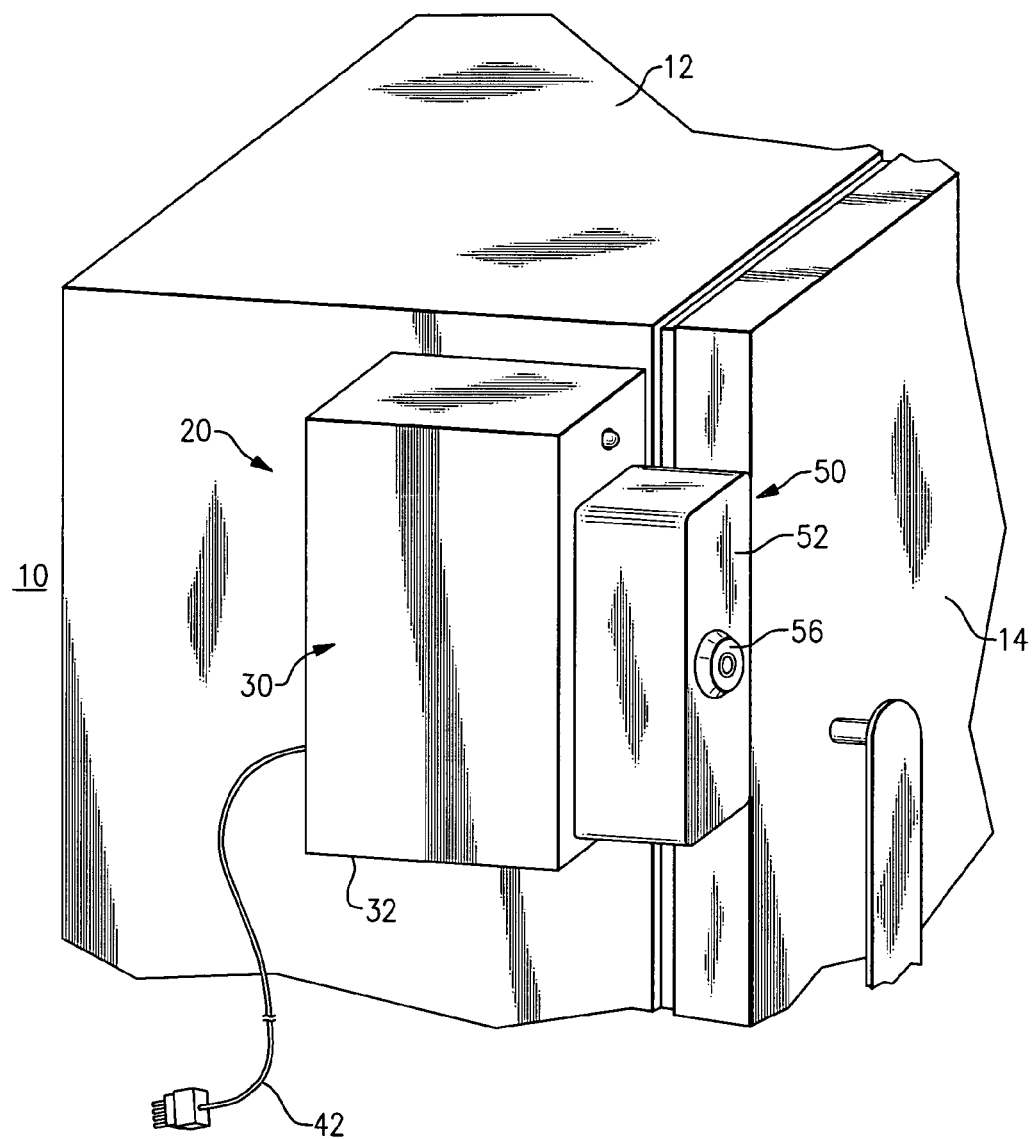
FIG. 2 is a perspective view of the embodiment.

With reference to the Drawing, and initially to FIGS. 1 and 2, a medication dispensing arrangement in a hospital or other health care facility employs one or more small refrigerators 10 in the patient rooms (or at the hubs of clusters of patient rooms) for storage and controlled access to medications and pharmaceuticals that need to be kept refrigerated. The refrigerator 10 has a cabinet body 12 and a door 14 that closes over the front of the cabinet body. In the illustrated embodiment, the door 14 is hinged at the right and opens from the left, but the refrigerator could as easily be a right-opening version. Typically, the door and cabinet have a magnetic closure of sufficient strength to maintain compression on the door seal. In this embodiment, the refrigerator has attached onto it a remote actuation door lock assembly 20, as described in more detail later. The door lock assembly is connected electrically or electronically via a network 22, e.g., a LAN, that makes either a wired or wireless connection with a hospital computer server 24, to which one or more work station computers 26, 26 are connected. The LAN 22 can also connect with door lock assemblies 20 for additional med storage refrigerators 10, here shown in broken line. These may be located in other patient rooms or in other locations throughout the facility.

Also shown here is a wall mounted medications cabinet 28, which may be mounted on the wall of the patient room in which the refrigerator 10 is located, and which is also coupled electronically with the hospital LAN 22. The purpose of the wall mounted cabinet 28 is to provide controlled access in the patient's room to non-refrigerated medications in one or more computer locked drawers. In this version, the cabinet 28 has an associated touch-screen computer 29 on which the nurse or other authorized health care provider can enter an authorization code to achieve access to the cabinet drawer(s). The same touch screen computer 29 may be used via the LAN 22 to release the lock mechanism on the refrigerator lock 20. Alternatively, the health care provider may employ a wireless hand-held device 100 that communicates with one of the computer work stations 26 to unlock the refrigerator lock 20.

In an alternative embodiment, e.g., in a physician's office, the refrigerator may be free standing, and have the lock 12 coupled to a local computer or to a small LCD device with a programmed microprocessor, which may be mounted on the refrigerator, for entering an unlock code to open the refrigerator, and which will keep an audit trail of the times of opening and closing.

Also, as shown in FIG. 1, the same door lock 20 may be applied onto a warming cabinet 110, which is intended to keep its contents at a temperature elevated above ambient, for example, at body temperature of 37° C. or 98.6° F. This may be used for storing radiology products, such as contrast materials that are to be injected into or ingested by a patient. These materials are considered pharmaceuticals, and must be kept under controlled conditions with access limited to certain individuals. The warming cabinet 110 has a door 112 secured to a cabinet body 114 with hinges 115 at the right and with the body portion 30 and door portion 50 of the door lock 20, here at the left side.

As shown in more detail in FIG. 2, the refrigerator door lock assembly 20 has two main components, namely, a body portion 30, with an enclosure or housing 32 that is affixed onto a side wall of the refrigerator cabinet body 12, and a door portion which has an enclosure or housing 52 that is affixed to an edge of the door 14, and which is aligned with the body portion 30. The body portion 30 and door portion 50 are shown here mounted on the left side wall of the cabinet body and left edge of the door, but the housing is adapted to be mounted on either the left or right side, depending on the side on which the refrigerator door opens.

An indicator LED 33 is shown here on the front wall of the body portion 30, to show the locked/unlocked status, and a USB cable 42 or ethernet cable extends from the body portion for attaching to the LAN 22 or otherwise to the remote computer, i.e., the hospital server 24. A key lock 56 is provided on the door portion 50 to permit the refrigerator lock to be unlocked manually, e.g., in the event of a power failure or computer system failure or outage.

The interior arrangements of the body portion 30 and door portion 50 of the refrigerator lock assembly are shown in more detail in FIGS. 3, 4, and 5.

Within the housing 32, the body portion 30 contains an electronics circuit board 34, which includes an ethernet port or USB port and suitably programmed controller microprocessor, which can be programmed to accept and/or transmit self-descriptive command data packets, so that the hospital computer system will assign each refrigerator lock assembly a unique identifier code. As is well known in the art, an interpretive communicative software driver within the hospital server 24 or other host computer contains and/or uses a library of pre-defined peripheral USB drivers to control the USB-based door lock assemblies. A customized USB driver engineered specifically for this refrigerator lock can also be uploaded onto the hospital server. A similar system is employed when ethernet or other network system is employed. The host computer assigns a unique code or serial number for each individual refrigerator door lock assembly 20. This permits the computer system to lock and unlock each of a large number of refrigerator door locks independently or one another.

The circuit board 34 also provides drive power to a servo motor and drive 36 for unlocking or releasing the door portion 50. In this embodiment, there is a transverse pivot pin 38 on which a latch lever 40 is pivoted for motion between a lower latched position (shown in solid) and a raised unlatched position (shown in ghost or broken line). The latch lever 40 has a slanting nose surface at its distal end, and a recess behind this for securing a latch strike plate 54 in the door portion 50. The slanting nose surface allows the lever to lift and then drops to latch and capture the strike plate when the refrigerator door closes.

The USB or ethernet cable 42 plugs into a suitable socket or jack on the circuit board 34. A serial-ethernet bridge interface may be used here. The host computer, e.g. hospital server 24, may use Windows, UNIX, LINUX or other suitable system. The system can employ a card reader, e.g., bar code or magnetic stripe, RFID, smart-card reader, or biometric device (e.g., fingerprint-, faceprint-, or retinal scanner) to provide access and unlock the lock assembly 20, in which case access may be by means of a card or badge carried by the health care provider. A suitable reader device could be installed within the medications cabinet 28 in the same room as the refrigerator.

The power for the latch motor servo can be provided from the USB port, or suitable DC can be obtained from the LAN to power the motor 36 (and also power the LED indicator 33 and sounder 35). Alternatively, an internal battery may be used in the body portion enclosure 32, or power can be derived from the associated refrigerator 10. An external DC power supply may also be used.

Also shown here are a temperature sensor 44 that is positioned in the interior of the cabinet body 12 and connects by wire to the circuit board 34. A humidity sensor 45 is located at the inside of the cabinet body, and is likewise wired to the circuit board 34. A magnetic proximity sensor is disposed at a front surface of the body portion 30, and is coupled to the circuit board 34 to provide an indication of the open/closed status of the door 14, which can then be communicated via the cable 42 and LAN 22 to the hospital computer system. The system can be programmed to alert the pharmacy personnel if one of the refrigerators fails to maintain a sufficiently cool interior temperature or if the relative humidity inside the cabinet is outside predetermined limits.

The LED lock/unlock status indicator 33 in this embodiment is adapted to glow red when the lock assembly 20 is locked, and to glow green when the lock assembly is unlocked. A no-glow or dark indication then indicates a fault or possible system failure. Flashing on-off intermittently can indicate, e.g., a temperature or humidity problem, i.e., that the sensor 44 or 45 has detected a high temperature condition or a high (or low) relative humidity.

An audible sounder 35 within the body portion housing 32 emits a tone or buzz if the refrigerator door remains open for a time that exceeds a predetermined time limit. The time limit can be programmed, e.g., from one of the work stations 26. The sounder alerts the nurse or other authorized attendant to close the refrigerator door, if the door has been inadvertently left open.

The distal end of the latch lever 40 protrudes out beyond the front wall of the body portion enclosure 32, and there is also an access opening at the rear wall of the door portion enclosure 52 to permit entry of the latch lever 40 so it can engage the strike plate 54. In this embodiment, the latch strike plate 54 is mounted on the key lock cylinder 56, so that the latch strike plate 54 can be rotated down and out of engagement with the latch lever, if necessary. This arrangement permits authorized personnel to open the refrigerator manually (with a key) in the event a power failure, network outage, or other event that might preclude obtaining electronic access.

Finally, a magnetic member 58 is situated in the door portion 50 and this is aligned with the magnetic proximity sensor 46 to close the sensor 46 when the door is closed. The proximity sensor 46 remains in its open state when the door is open and the magnetic member is not in proximity.

Other arrangements employing the same general principles can be used in other environments where there is a need to control access to the contents of the refrigerator. One possibility is in connection with a weight control program where access to food is limited to meal times so as to prevent or discourage snacking. Another possibility is in a hospitality environment, where access to reserve supply refrigerators in hospitality suites are to be limited to authorized hotel staff or catering personnel.

In a preferred embodiment, the hospital computer system keeps track of the times each refrigerator is unlocked, and the of identities of authorized personnel who obtain (or attempt to obtain) access, i.e., the system creates an audit trail of health providers who request access.

Figure 6:
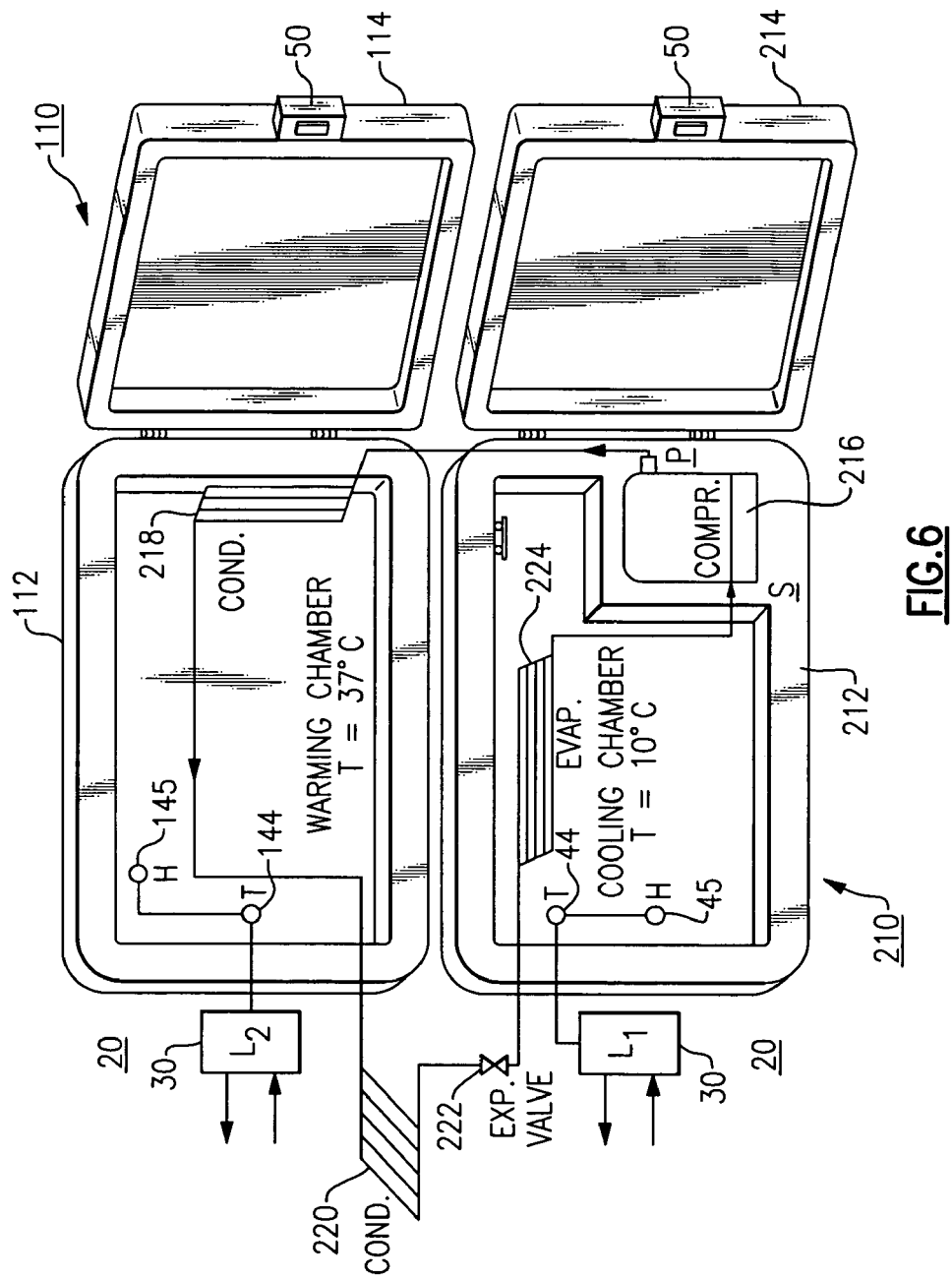
FIG. 6 is a perspective view of an alternative embodiment.

FIG. 6 illustrates one possible alternative arrangement, in which there is a combined pharmaceutical refrigerator and warming cabinet with separate compartments for cool storage and warm storage, and with respective door locks for each. Elements that have been previously described in respect to a prior embodiment are identified with similar reference numbers, but raised by 100, 200, 300, 400 or 500, as the case may be. In this embodiment there is an upper warming compartment 110, with a cabinet body 112 and door 114 that is hinged at the right side. An upper door lock 20 has its body portion 30 affixed onto the cabinet body 112 and has its door portion 50 affixed onto the warming compartment door 114. Beneath this is a refrigerator compartment 210 with a refrigerator cabinet body 212 and door 214, also hinged at the right, and with a lower door lock 20 with the body portion 30 and door portion 50 affixed to the cabinet body 212 and door 214, respectively. In this example, there is a single refrigerant circuit used for cooling the refrigerator compartment 210 and also heating the warming compartment 110. A compressor 216 supplies compressed refrigerant from a pressure port P to a first condenser 218 located inside the warming compartment cabinet 112. The refrigerant then flows to a supplemental external condenser 220, and from there through an expansion valve 222 to an evaporator coil 224 inside the cooling compartment body 212. The refrigerant vapor then returns to a suction port S of the compressor 216. A supplemental electric heater may be used in the warming compartment.

As shown in FIG. 7, the refrigerator door lock can be applied in a mobile or portable implementation. In this example, a mobile or transportable refrigerated storage chest 410 is used for transport of medications under controlled conditions of temperature and humidity. The chest has a body portion 412 and an upper door or lid 414, here shown hinged at the right. A door lock 420 has its body portion 430 attached to the chest body 412 and has its door portion 450 affixed to the front edge of the door or lid 414, and aligned with one another. There is an on-board touch screen computer controller 429 affixed onto the storage chest, and connected by cable to the lock 420, permitting a trusted or authorized person to gain access to the chest and to its contents. Access can be by entry of code, or by identification of a bar code or magnetically coded card, or by an RFID identification badge or card, for example. The computer controller 429 can maintain an audit trail of times and persons having access, and can also maintain a log of the temperature and humidity inside the storage chest. In this embodiment, the lock 420 is modified to work on internal battery power (e.g., from a small battery B mounted on the printed circuit board 34 of FIG. 3), or can be powered via cable from the touch screen computer controller 429. This creates the ability for the device to monitor pharmaceuticals when in transport, even when the chest is not connected to an external power supply. If the temperature or humidity was out of the acceptable range during shipping, the lock 420 would be programmed to deny access to the chest or container holding the pharmaceuticals, to prevent the distribution of potentially tainted medication. Authorized pharmaceutical supervisory personnel would have an access code to allow them to retrieve the contents. The storage chest 410 can be a passive container, or alternatively may employ any suitable mechanism to maintain the proper temperature and humidity conditions, e.g., a solid-state Peltier cycle device or a system employing a refrigerant fluid. The touch screen computer controller 429 can be wirelessly connected with a local or wide area network, to permit remote monitoring or to provide access from a remote station. Where the transport chest is a passive container, it will rely on the environment in which it is located (e.g., refrigerated car or trailer) to maintain the proper temperature and humidity conditions. If the temperature or humidity is outside the acceptable range, the lock will not permit opening by a staff member. A supervisor with a special override code would be needed to access the container.

A stand-alone or free-standing refrigerator 510 that employs a door lock 520 of this invention is shown in FIG. 8. Here, the lock body portion 530 is affixed onto the refrigerator cabinet 512, and the lock door portion 550 is affixed onto the refrigerator door 514. A local computer device, i.e., a touch-screen control and display interface device 529, is also mounted on one side of the refrigerator cabinet 512. Alternatively, this or a similar device can be affixed to or incorporated into the lock body portion 530. In some cases, the device 529 can be remoted to a nearby cabinet or wall space. The touch-screen device 529 is coupled to the circuit board within the body portion 530. The touch-screen device 529 (or the lock body portion 530) may optionally be connected by USB cable, ethernet, wireless device, or other means to another computer or to a network.

In this arrangement, the touch-screen device 529 has a display panel 531, shown in more detail in FIG. 9. A keypad 532 is formed on this panel 531, having number keys for entering data and codes, as well as ENTER and CLEAR keys. A temperature display area 533 shows the temperature within the refrigerator cabinet 512. This can be configured to flash on and off if the temperature is too low or too high. A lower portion 534 of the screen can indicate the OPEN/CLOSED status and LOCKED/UNLOCKED status. An optional relative humidity display area 535 shows the humidity level within the cabinet 512.

The device 529 may be programmed to keep an audit history of all persons (and times) accessing the pharmaceutical refrigerator. The device may also keep a history of the temperature and humidity conditions within the refrigerator cabinet. The temperature and humidity charts may be displayed on the screen 531.

This embodiment provides quiet operation. There may be a bar-code scanner and/or RFID reader or badge reader, that can be employed for gaining authorized access. The lock mechanism is self-locking. The lock device remains locked during power outages (except by key access) for security and to maintain temperature conditions within the cabinet. The audit history feature can provide the time of opening the refrigerator, identity of the person provided access, temperature (and humidity) level(s) within the refrigerator cabinet, and a record of what drugs were removed (employing the bar-code reader option). If the unit is networked, this feature can interface with an inventory system as to which items have been dispensed.

The temperature sensor feature provides continuous readings of refrigerator cabinet temperature. If the temperature strays outside of a settable acceptable range, standard users will be locked out from electronic access, to prevent dispensing of improperly stored drugs. This provides a critical layer of patient protection from potentially contaminated medications.

The refrigerator lock as describe hereinabove can be employed with an insulated shipping container or crate for shipping refrigerated drugs which need to be maintained within a safe temperature range. These crates may contain ice to maintain a cool internal temperature, or may be shipped within a refrigerated container or refrigerated chamber. In this case, different size boxes may be used for different size shipments, and access to the contents is obtained by opening a hinged top or hinged side. The hinged top (or side) incorporates an lock with temperature and/or humidity monitoring. The means for setting the lock would be inside the shipping box and not accessible from outside and unable to be tampered with from outside. The lock has programmable windows for acceptable temperature and humidity, and logs temperature and humidity as a means of creating an audit history for the shipment. The lock, as described earlier, would preferably have electronic locking, and would be battery powered, with a provision for key lock over-ride. If the lock detects that the temperature (and/or humidity) has been outside the acceptable range during the transit, the lock denies electronic access, i.e., creates a lock-out condition. The lock should have a means of entering an access code, e.g., a keypad and an LCD display, although this may be omitted where the recipient can plug in a local PC or PDA, e.g., using a USB connection, to gain access.

Of course, the lock may also be employed without the temperature and humidity features for secure shipments of narcotics or other controlled substances.

When the shipment arrives at the destination, the recipient must first obtain a security-generated ID code from the box lock. This ID code is then entered into a shipper website. If the ID code represents a transport in which the temperature and humidity were acceptable, the website will return a password that allows the lock to release and allows the crate to be opened. However, if the generated ID code indicates a shipment where the transport did not meet safe temperature and humidity specifications, the website will notify the recipient (as well as the shipper) that the medicine is presumed tainted, and will not allow the recipient of the crate to open the container. The website also instructs the recipient as to the next step, i.e., to return the crate immediately to the pharmaceutical company. Then when the shipper receives the box in the return shipment, the shipper will be able to open the crate (using an over-ride passcode or a manual pass key) to inspect the contents.

This process ensures that a secure transport chain is maintained, protecting the integrity of the medications at all times.

If it turns out that the shipment without the proper ID code is not returned, or is returned with indication of damage from forced opening, the pharmaceutical company and the governmental authorities would know that a batch of medication was tainted and was still distributed and used. The company can then send out warnings to users that certain date-coded and/or lot-coded medications may be tainted and are not to be used.

In addition, at time of shipment, the information on the packing list (i.e., contents, including lot numbers) preferably can also be entered into the aforementioned website. The website would then generate a "locking" code for the container: this code would be different from the unlock code, but software in the container electronics would be able to use this to generate a unique time-sensitive unlock code which would be released from the website when the correct ID is entered as input. This code can be entered into the container manually, or via a USB connection to an Internet-connected PC. If a faulty or incorrect ID code is entered (after some limited number of attempts) the box will need to be returned to the sender for manual unlocking. At the sender location, the USB connection can be employed for download of audit trail information, and can identify the time, location, and nature of the problem in transport.

The box itself can be fabricated of a durable plastic or metal (e.g., aluminum) to keep weight and shipping costs down. The box may contain insulation plus room for ice and the medications. Alternatively, the box may have air holes for ventilation for use in a refrigerated truck. The box may have an isolated ice or freezer pack compartment. The battery power may be from standard alkaline batteries, or from rechargeable cells, which may potentially be recharged via the USB connection.

This shipping box with lock achieves control over the transport chain, using Internet access. By mandating proper entry of a code to a secure website, with the user being unable to open the box without accessing this website, the box and lock guarantees reporting of improper transport and possibly tainted medications. The timing of the input also helps assure that the medication was delivered in timely fashion, and that there were no shipping delays in transit where the product was unrefrigerated.

The lock of this invention can also be used in shipping of controlled materials, e.g., narcotics, where temperature and humiditity do not need to be monitored, but where it important to ensure against tampering or unauthorized openings of the cabinet. In this case, the lock includes a battery power supply, and the control circuit within the lock body incorporates suitable software with a provision for accepting an opening code from an authorized user so as to enable the motor drive mechanism to move the latch member from engagement so that the cabinet can be opened. Also, the software which includes an audit trail provision for recording a history of the times and identities of person(s) opening the cabinet. Preferably, the on-board software on the cabinet lock suitable software includes a provision to create an ID code that is displayed to an authorized recipient of the shipping cabinet. The contents encoded within the ID code will identify whether there has been tampering or unauthorized opening of the cabinet, so that the recipient returns the ID code to the shipper (e.g., via Internet) to obtain the opening code for the lock only if there has been no tampering and no unauthorized openings. Then, the shipper returns the opening code, and the authorized recipient can open the cabinet. However, if the ID code indicates that the tampering or unauthorized opening has occurred, the shipper will not provide the opening code, but instead will provide instructions to secure and/or return the cabinet. The shipper software can be programmed to automatically inform the appropriate government authorities of a possibly compromise of the controlled substance.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

I claim:

1. A portable or mobile controlled temperature shipping cabinet and door lock therefor, wherein the shipping cabinet has a cabinet body in which temperature sensitive materials are to be stored and a door which closes against said cabinet body, the door lock having a body portion that mounts onto the cabinet body and a door portion that mounts onto the door to align with the body portion when the storage cabinet door is closed;

the door portion comprising
an enclosure that mounts to the door; and
a latch strike member within said enclosure;
the body portion comprising
an enclosure mounting to the cabinet body;
a latch member to engage said latch strike member;
a motor drive mechanism for selectively moving said latch member from engagement with said latch strike member to unlock the cabinet;
suitably programmed circuit means within the enclosure of the body portion for receiving commands specific to the door lock to actuate said motor drive to move the latch member out of engagement with said latch strike member; and
a battery power supply; and
a temperature monitor having a probe sensing temperature inside said cabinet, the monitor being coupled with said suitably programmed circuit means for communicating said temperature thereto; further comprising
a humidity monitor having a probe sensing a humidity level inside said shipping cabinet, the monitor being coupled with said suitably programmed circuit means for communicating said humidity level thereto;
suitable software operative to prevent the motor drive from lifting said latch member out of engagement when said the temperature detected by said temperature monitor is outside a predetermined range; and
wherein said suitable software includes a provision for providing an ID code to a recipient of the shipping cabinet, wherein the ID code will identify whether the temperature detected by the temperature monitor has been outside the predetermined temperature range and whether the humidity detected by the humidity monitor has been outside a predetermined humidity range; and wherein the recipient returns the ID code to the shipper to obtain an opening code for the lock and if the ID code indicates that the temperature and humidity have been maintained within the respective ranges, the shipper will provide the opening code, but if the ID code indicates that the temperature or the humidity has been outside the associated range, the shipper will not provide the opening code.

2. A portable or mobile controlled temperature storage cabinet and door lock therefor according to claim 1, further including software which includes audit trail means for recording a history of the temperature as detected by the temperature monitor.

* * * * *